United States Patent
Miller et al.

(10) Patent No.: US 11,464,427 B2
(45) Date of Patent: Oct. 11, 2022

(54) CUSTOM FOOT ORTHOTIC AND SYSTEM AND METHOD FOR DESIGNING OF A CUSTOM FOOT ORTHOTIC

(71) Applicants: Steven Miller, Charlottetown (CA); Todd McLean, Charlottetown (CA)

(72) Inventors: Steven Miller, Charlottetown (CA); Todd McLean, Charlottetown (CA); Patrick Connor, Mount Stewart (CA)

(*) Notice: Subject to any disclaimer, the term of this patent is extended or adjusted under 35 U.S.C. 154(b) by 0 days.

(21) Appl. No.: 16/496,071

(22) PCT Filed: Mar. 22, 2018

(86) PCT No.: PCT/CA2018/050348
§ 371 (c)(1),
(2) Date: Sep. 20, 2019

(87) PCT Pub. No.: WO2018/170600
PCT Pub. Date: Sep. 27, 2018

(65) Prior Publication Data
US 2020/0060580 A1    Feb. 27, 2020

Related U.S. Application Data

(60) Provisional application No. 62/601,417, filed on Mar. 22, 2017.

(51) Int. Cl.
    G05B 19/4099 (2006.01)
    A61B 5/103 (2006.01)
    A61B 5/107 (2006.01)

(52) U.S. Cl.
    CPC .......... *A61B 5/1038* (2013.01); *A61B 5/1036* (2013.01); *A61B 5/1074* (2013.01);
    (Continued)

(58) Field of Classification Search
    CPC ... A61B 5/1038; A61B 5/1074; A61B 5/1036; G05B 19/4099; G05B 2219/49007; G05B 2219/35134
    (Continued)

(56) References Cited

U.S. PATENT DOCUMENTS

2006/0070260 A1*  4/2006  Cavanagh ............ A61B 5/1036
                                                        36/44
2007/0245504 A1   10/2007  Spector
(Continued)

FOREIGN PATENT DOCUMENTS

| CN | 106420144 A | 2/2017 |
| EP | 2708211 A1 | 3/2014 |
| KR | 101600498 B1 | 3/2016 |

OTHER PUBLICATIONS

Written Opinion for PCT application No. PCT/CA2018/050348, CIPO, dated May 22, 2018.
(Continued)

*Primary Examiner* — Michael W Choi
(74) *Attorney, Agent, or Firm* — Bhole IP Law; Anil Bhole; Marc Lampert

(57) ABSTRACT

A custom foot orthotic and a system and a method for designing of a custom foot orthotic. The method includes: receiving 3D scan data of the patient's foot; receiving plantar pressure scan data of the patient's foot; establishing a desirable pressure distribution; generating an underfoot elevation profile relative to an elevation profile of the patient's foot in the 3D scan data; determining an internal density profile of the resulting foot orthotic 3D model by superimposing the desirable pressure distribution over the resulting foot orthotic 3D model and reducing or increasing density in regions of the foot orthotic 3D model based on the difference between an expected pattern of support and the
(Continued)

desirable pressure distribution; and outputting the 3D model of the custom foot orthotic.

25 Claims, 10 Drawing Sheets

(52) U.S. Cl.
CPC ............... *G05B 19/4099* (2013.01); *G05B 2219/35134* (2013.01); *G05B 2219/49007* (2013.01)

(58) Field of Classification Search
USPC .......................................................... 700/98
See application file for complete search history.

(56) References Cited

U.S. PATENT DOCUMENTS

| | | | |
|---|---|---|---|
| 2009/0183390 A1 | 7/2009 | Miller et al. | |
| 2016/0331071 A1* | 11/2016 | Kane | A43D 1/02 |
| 2017/0255185 A1* | 9/2017 | Hinshaw | G06N 5/022 |
| 2018/0229446 A1* | 8/2018 | Bastian | B29C 64/386 |

OTHER PUBLICATIONS

International Search Report for PCT application No. PCT/CA2018/050348, CIPO, dated May 22, 2018.

* cited by examiner

CUSTOM FOOT ORTHOTIC AND SYSTEM AND METHOD FOR DESIGNING OF A CUSTOM FOOT ORTHOTIC

TECHNICAL FIELD

The present disclosure generally relates to orthotics. More particularly, the present disclosure relates to a custom foot orthotic and a system and a method for designing of a custom foot orthotic.

BACKGROUND

Foot orthotics, also called shoe inserts or foot orthoses, are devices commonly used to provide comfort under a patient's foot, provide foot and joint pain relief, prevent injuries, provide orthopedic correction, or the like. In some cases, foot orthotics can be inserted into the patient's shoe as a "shoe insert". In other cases, the foot orthotic can be comprised out of the undersole of the patient's shoe. In some cases, the foot orthotic can be customized to the shape of the patient's foot. However, with conventional foot orthotics, even where there is customization of the foot orthotic, there is typically an overreliance on subjective opinion, and thus the foot orthotic is not as effective.

It is therefore an object of the present invention to provide a custom foot orthotic, and a method of production of such custom foot orthotic, in which the above disadvantages are obviated or mitigated, and attainment of desirable attributes is facilitated.

SUMMARY

In an aspect, there is provided a system for designing of a custom foot orthotic for a patient, the system in communication with a plantar pressure sensor array, an input device, and an output device, the system comprising one or more processors and a data storage device, the one or more processors configured to execute: a pressure data module to receive plantar pressure scan data of the patient's foot from the plantar pressure sensor array and to establish a desirable pressure distribution; a model generation module to determine an internal density profile of a resulting foot orthotic 3D model by superimposing the desirable pressure distribution over the resulting foot orthotic 3D model and reducing or increasing portions of a density distribution over the foot orthotic 3D model based on the difference between an expected pattern of support and the desirable pressure distribution; and an output module to output the resulting 3D model of the custom foot orthotic to the output device.

In a particular case, the system is in further communication with a 3D scanner, the one or more processors further configured to execute a scanning data module to receive 3D scan data of the patient's foot from the 3D scanner, and wherein the model generation module further generates an underfoot elevation profile relative to an elevation profile of the patient's foot in the 3D scan data.

In another case, the model generation module determines the resulting foot orthotic 3D model of the custom foot orthotic by removing an area corresponding to the underfoot elevation profile from a base orthotic shape.

In yet another case, the expected pattern of support is determined using a physical simulation, where physical properties are used to generate a map of upward forces applied by the surface of the orthotic onto the foot, the physical properties comprising physical properties of a generalized foot and material properties of the orthotic.

In yet another case, the one or more processors further configured to execute an input module to receive one or more input parameters from an operator via the input device, the one or more input parameters comprising a selection of the base orthotic.

In yet another case, the one or more input parameters further comprise the desirable pressure distribution to be established.

In yet another case, adjustments to the desirable pressure distribution are received by the input module from the operator via the input device.

In yet another case, the plantar pressure sensor array is associated with a walkway, and wherein the plantar pressure scan data is a composite of multiple foot pressure readings received while the patient was walking on the walkway.

In yet another case, the plantar pressure sensor array is associated with a platform, and wherein the plantar pressure scan data is a composite of multiple foot pressure readings received while the patient was standing on the platform.

In yet another case, the output device is a 3D printing device that produces a physical manifestation of the 3D model of the custom foot orthotic.

In yet another case, the 3D printing device uses Fused Deposition Modeling to modify infill densities of the physical custom orthotic according to the internal density profile of the 3D model of the custom foot orthotic.

In yet another case, the desirable pressure distribution is an average plantar pressure distribution calculated over a plurality of sample patients, the average plantar pressure distribution being pressure-scaled and fitted to the patient's plantar pressure scan data.

In another aspect, there is provided a computer-implemented method for designing of a custom foot orthotic for a patient, the method comprising: receiving plantar pressure scan data of the patient's foot; establishing a desirable pressure distribution; determining an internal density profile of the resulting foot orthotic 3D model by superimposing the desirable pressure distribution over the resulting foot orthotic 3D model and reducing or increasing density in regions of the foot orthotic 3D model based on the difference between an expected pattern of support and the desirable pressure distribution; and outputting the 3D model of the custom foot orthotic.

In a particular case, the method further comprising receiving 3D scan data of the patient's foot and generating an underfoot elevation profile relative to an elevation profile of the patient's foot in the 3D scan data.

In another case, the method further comprising determining a resulting foot orthotic 3D model of the custom foot orthotic by removing an area corresponding to the underfoot elevation profile from a base orthotic shape.

In yet another case, the expected pattern of support is determined using a physical simulation, where general physical properties of foot elasticity and physical properties of the orthotic material are used to generate a map of upward forces applied by the surface of the orthotic onto the foot.

In yet another case, the internal density profile is determined by iteration via successively comparing the physical properties of a current expected pattern of support to the desirable pressure distribution until the last iteration does not provide a substantially better match between the current expected pattern of support and the desirable pressure distribution than a previous iteration.

In yet another case, the method further comprising receiving one or more input parameters from an operator, the one or more input parameters comprising a selection of the base orthotic.

In yet another case, wherein the one or more input parameters further comprise the desirable pressure distribution to be established.

In yet another case, the method further comprising receiving adjustments to the desirable pressure distribution from an operator.

In yet another case, the plantar pressure scan data is a composite of multiple foot pressure readings received while the patient was walking.

In yet another case, the plantar pressure scan data is a composite of multiple foot pressure readings received while the patient was standing.

In yet another case, determining the resulting foot orthotic 3D model of the custom foot orthotic comprises: virtually positioning and aligning the underfoot elevation profile to a surface of the base orthotic shape; virtually lowering the underfoot elevation profile along the vertical 'Z' axis below the surface of the base orthotic such that the underfoot elevation profile at least partially resides inside of the base orthotic shape; and removing areas of the base orthotic shape that encompass the same space as the underfoot elevation profile.

In yet another case, positioning and aligning the underfoot elevation profile comprises: virtually positioning 'X' and 'Y' coordinates of a geometric center of the underfoot elevation profile at the same location as 'X' and 'Y' coordinates of a geometric center of the base orthotic shape; and virtually rotating and shifting the underfoot elevation profile or the base orthotic shape along respective 'X-Y' planes until the underfoot elevation profile overlaps the base orthotic and the gap between the perimeter of the underfoot elevation profile and the perimeter of the base orthotic is substantially proportionally uniform along the length of the perimeter of the underfoot elevation profile.

In another aspect, there is provided a custom foot orthotic customized to a patient and produced using a manufacturing environment based on a 3D model of the custom foot orthotic, the 3D model generated by one or more processors configured to execute: a scanning data module to receive 3D scan data of the patient's foot from a 3D scanner; a pressure data module to receive plantar pressure scan data of the patient's foot from a plantar pressure sensor array and to establish a desirable pressure distribution; a model generation module to generate an underfoot elevation profile relative to an elevation profile of the patient's foot in the 3D scan data, the model generation module further determines an internal density profile of the resulting foot orthotic 3D model by superimposing the desirable pressure distribution over the resulting foot orthotic 3D model and reducing or increasing density in regions of the foot orthotic 3D model based on the difference between an expected pattern of support and the desirable pressure distribution; and an output module to output the 3D model of the custom foot orthotic to the manufacturing environment for production of the custom foot orthotic.

These and other embodiments are contemplated and described herein. It will be appreciated that the foregoing summary sets out representative aspects of systems and methods to assist skilled readers in understanding the following detailed description.

BRIEF DESCRIPTION OF THE DRAWINGS

Preferred embodiments of the present disclosure will now be described, by way of example only, with reference to the attached Figures, wherein.

DETAILED DESCRIPTION

Figure 1:
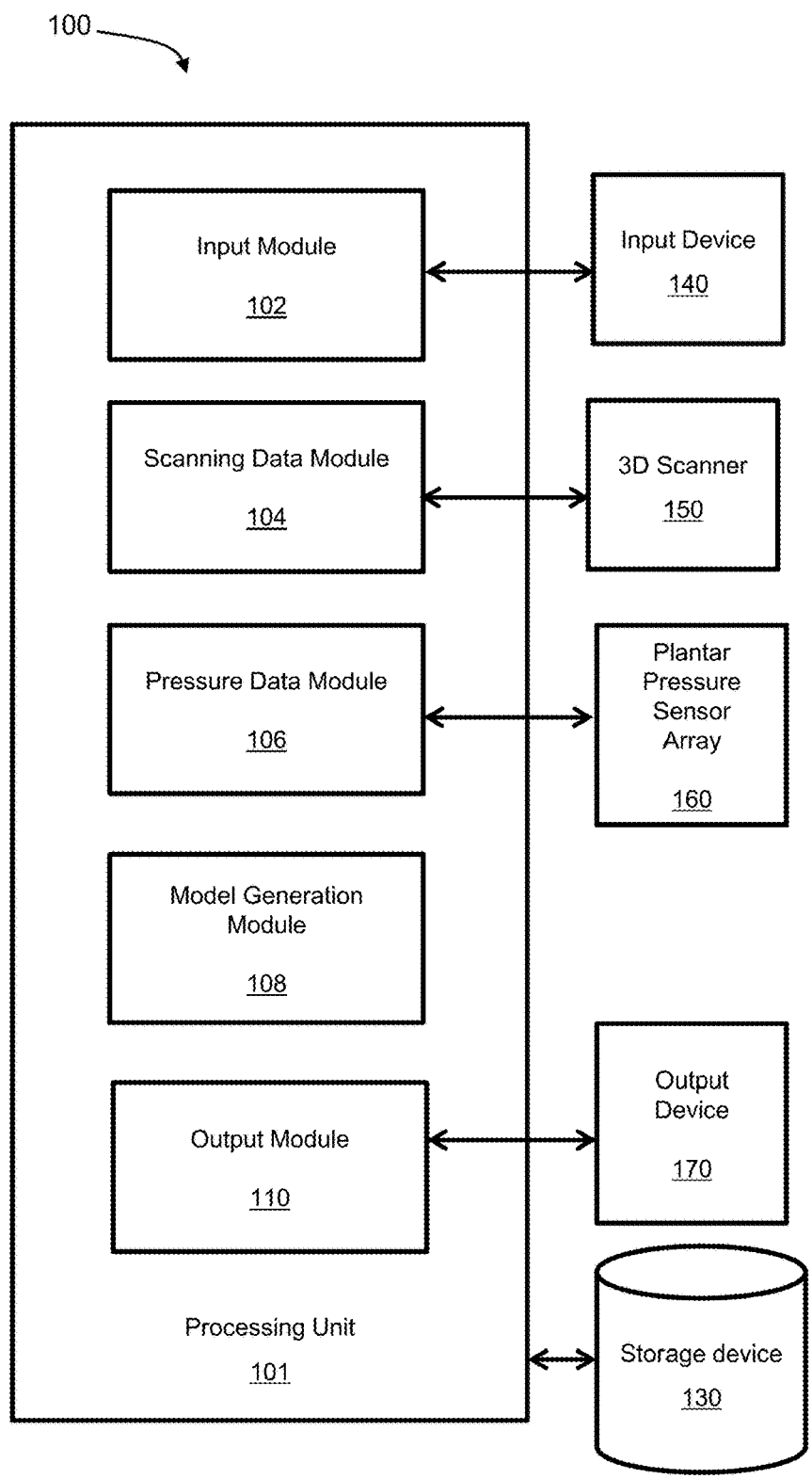
FIG. 1 is a diagram of a system for designing of a custom foot orthotic, in accordance with an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to foot orthotics. More particularly, the present disclosure relates to a custom foot orthotic and a system and a method for designing of a custom foot orthotic.

In some cases, foot orthotics are produced from molds of a patient's feet. There are several approaches to creating the basis for such molds; for example, plaster casts, foam box impressions, or three-dimensional (3D) computer imaging. Each approach having varying levels of accuracy.

In many cases, foot orthotics are designed with static input. The data acquired may not consider functional forces such as momentum vectors (weight bearing in motion) during human movement and gait. In this way, corrections are generally made for mechanical alignment rather than kinematic correction, the corrections are non bio-mechanical in that they correct the foot in isolation. As an example, a mal-alignment at the foot may be mitigated or potentiated by the superior joint(s), and thus can affect the actual functional deformity. Correction solely at that level of the foot would generally not take into account any issues remote from that area.

Conventionally, aspects of orthotics production might be considered more of an art than a science. Corrections that are greater than a standard contour map are generally created by an expert or professional practitioner using subjective input factors. This subjective variability and potential error can cause issues for patients. There are many instances where expensive custom orthotics, developed by highly-skilled professionals, were determined to be ineffective for their intended purpose. This ineffectiveness may be due to reliance on subjective experience in the absence of information about the underfoot pressure distribution during walking or standing. Additionally, there is no way to verify the effectiveness of the orthotic before manufacture. Thus, ineffectiveness may be because there is no practical feedback loop to correct deficiencies, leading to unsatisfactory results.

The embodiments described herein advantageously provide an objective, effective, simple to operate, and pre-fabrication testable approach to the design of custom orthotics.

In a particular approach, 3D scanning technology can be used to determine a life-size 3D foot shape of the underside of the patient's foot. The 3D scan data can then be used to fashion an orthotic that is contoured to the patient's foot. In some cases, the system can choose thickness at each point in the orthotic to correspond to the foot shape. In further cases, the density at each point in the orthotic material can be chosen according to the patient's foot shape. In another approach, the 3D scanned foot shape can be used to select an appropriate base orthotic according to the outline of the 3D foot shape. In this approach, on a computer display, the foot shape and plantar (underfoot) pressure data can be superimposed to help an operator or professional decide where to make a change in the shape of the orthotic to relieve high-pressure stress on the foot. These approaches generally involve a strategic change in the elevation or thickness of the orthotic at one or more locations of the orthotic. Generally, these approaches require an operator with some expert knowledge or experience for producing the orthotic to achieve the desired results, such as to relieve stress, offload pressure points, and/or correct angular deformities.

The embodiments described herein advantageously provide an automated, data-driven approach to producing an orthotic that considers the foot shape and plantar pressures to consistently provide a desirable fit and function for the patient.

The embodiments described herein provide a way of combining 3D scanned foot shape data and sensed plantar pressure data to automatically adjust density and elevation of a selected base orthotic to achieve a desirable underfoot pressure distribution. The 3D scanner is used to capture a life-sized 3D model of the patient's underfoot surface. The scanned 3D foot shape is used as input to automatically determine an elevation or thickness of the orthotic relative to an insole of a patient's host shoe. The 3D scan of the patient's foot can be from any suitable 3D Scanner. For example, 3D scanners that collect a set of 3D points on real-world surfaces by, for example, measuring the time it takes for light to travel from the device to the surface and back (i.e., time of flight). The 3D points can then be arranged to form a surface or 3D model of a real-world object. In a particular case, the 3D scanner can be the Microsoft™ Kinect™ platform.

The sensed plantar pressure data can be acquired from an array of plantar pressure sensors or from plantar pressure measurement devices (also sometimes called pressure mats or pressure sensing flooring). The sensed plantar pressure data can be acquired while the patient walks or stands on a high-resolution plantar pressure measurement device. The sensed plantar pressure data can be used to adjust internal density across the orthotic, whereby high-pressure areas have relatively lower densities and vice versa.

In some cases, an operator can select from one or more desirable underfoot pressure distributions and manually adjust the automatically generated distribution as necessary. Achieving this desirable pressure distribution of underfoot pressures generally becomes a target of the orthotic production and design. In further cases, the desirable pressure distribution may be fixed, for example, to encourage a uniform expected pattern of support in the custom orthotic.

In some cases, the density distribution across the orthotic can be iteratively adjusted to enhance the orthotic's expected pattern of support. In some cases, this can be accomplished via simulation, using a virtual model of the fabricated orthotic and the patient's foot shape and plantar pressure data, to match the desirable pressure distribution. Production of such an orthotic can be accomplished using fabrication technology that is capable of adjusting the density of the orthotic material; for example, Fused Deposition Modeling 3D printing can be used by allowing variable-sized voids on the interior of a completed 3D print.

In some cases, the operator can preview an orthotic model, and an expected pattern of support provided by the orthotic, pre-fabrication; i.e., prior to initiating the production of the orthotic.

Referring now to FIG. 1, a system for designing of a custom foot orthotic 100 is shown. The system 100 includes a processing unit 101, an input device 140, a storage device 130, a 3D scanner 150, a plantar pressure sensor array 160, and an output device 170. The input device 140 can be any device or interface that receives information from a user; for example, a keyboard, a mouse, a touchscreen, or the like. The output device 170 can be any device that provides information to the user; for example, a monitor, a display, speakers, or the like. In some cases, the input device 140 and the output device 170 can be can be the same device; for example, a touchscreen display. The processing unit 101 may be communicatively linked to the storage device 130, which may be preloaded, periodically loaded, and/or continuously loaded with data obtained from the 3D scanner 15 and/or the plantar pressure sensor array 160. The processing unit 101 includes various interconnected elements and modules, including an input module 102, a scanning data module 104, a pressure data module 106, a model generation module 108, and an output module 110. The scans captured by the 3D scanner 150 can be processed by scanning data module 104 and stored on the storage device 130. The sensor data captured by the plantar pressure sensor array 160 can be processed by pressure data module 106 and stored on the storage device 130. In further embodiments, one or more of the modules can be executed on separate processing units or devices, including the input device 140, the storage device 130, the 3D scanner 150, the plantar pressure sensor array 160, or the output device 170. In further embodiments, some of the features of the modules may be combined or run on other modules as appropriate.

In some cases, the processing unit 101 can be located on a computing device that is remote from one or more of the input device 140, the storage device 130, the 3D scanner 150, the plantar pressure sensor array 160, or the output device 170; for example, a local-area network (LAN), a wide-area network (WAN), the Internet, or the like. In some cases, the processing unit 101 can be executed on a centralized computer server, such as in off-line batch processing. The system 100 advantageously provides rapid, data-driven design of custom orthotics.

Figure 2:
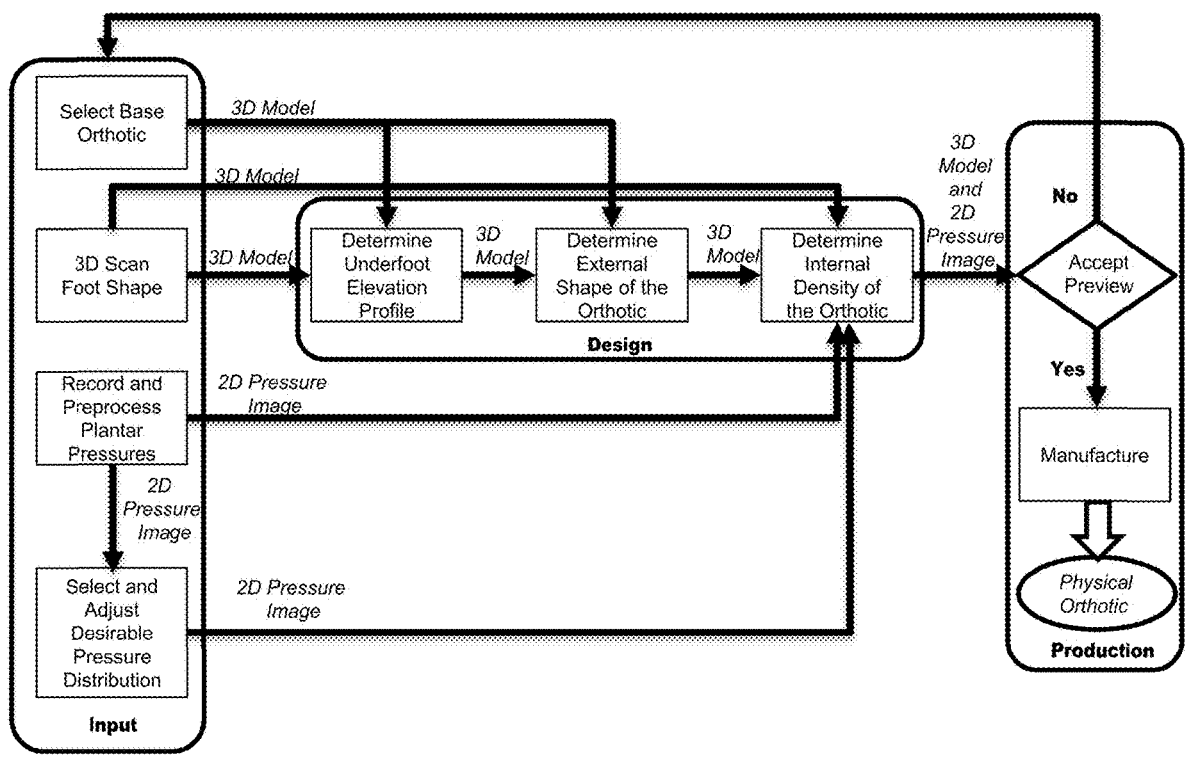
FIG. 2 is a diagram showing exemplary data interactions and data flow of the system of FIG. 1.

Turning to FIG. 2, data interactions and data flow of the system 100 is diagrammatically depicted. The 3D scanner 150 and the plantar pressure measurement device 160 provide input to the processing unit 101. The input device 140 provides an operator a way of interacting with the system 100 by allowing the operator to provide input, and in some cases, select and adjust elements used in the design. The output device 170 allows the operator to view an orthotics design generated by the system 100 and, in some cases, the generated orthotic design's expected behavior. In some cases, the output device 170 can be a manufacturing environment, for example a 3D printer or a computer numerical control (CNC) machine, that manufactures the orthotic based on a final 3D orthotic model outputted by the system 100. The output device 170 may be located remotely from the rest of the system 100.

Figure 10:
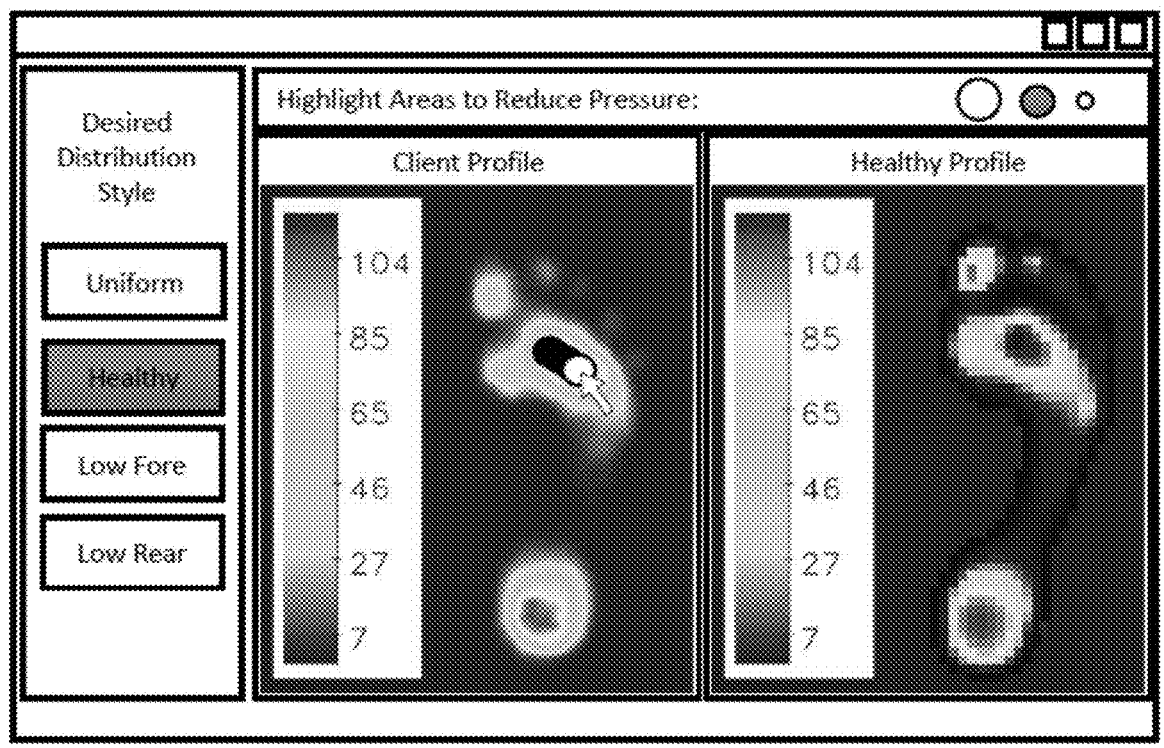
FIG. 10 illustrates an exemplary screenshot of an interface for selecting and adjusting a desirable underfoot pressure distribution.

The data interactions of FIG. 2 can be divided into three conceptual stages: input, design, and production. In the input stage, the operator performs both the 3D foot shape scan with the 3D scanner 150 and the plantar pressure scan with the plantar pressure sensor array 160. In some cases, via the input device 140, the operator can select a base orthotic design according to the type of host shoe into which the finished custom orthotic will be inserted or the type of shoe of which the custom orthotic will comprise the sole. In some cases, the operator can also select and adjust the desirable underfoot pressure distribution, taking input from, for example, the plantar pressure recording and patient reports of discomfort in specific foot areas. FIG. 10 illustrates an exemplary screenshot of an interface for adjusting the desirable underfoot pressure distribution. In the design stage, the model generation module 108 combines the operator inputs, including the desired pressure distribution, to automatically generate a model of a custom orthotic. In the production stage, in some cases, the operator can preview the generated model, and expected pattern of support provided by the custom orthotic, before the system 100 directs the output device 170 to manufacture the orthotic. In the present embodiments, although example hardware and software instantiations are sometimes described as separate entities, it is contemplated that an integration of such components can be used.

In order to select and adjust the desirable underfoot pressure distribution, depending on a desired type of comfort or functional correction, the operator can select a "base" underfoot pressure distribution. If the patient requests general comfort, the operator may select a "uniform" pressure distribution, where the resulting orthotic would be aimed to evenly distribute pressure over substantially all parts of the foot. However, if the patient wants to correct a particular issue, the operator may opt instead to use a "healthy" distribution, where the goal is to produce an orthotic that shifts pressures to the areas where they are normally experienced during a healthy step or stance. Other "base" underfoot pressure distributions are contemplated; for example, where the patient desires low pressure in the heel or in the forefoot. In this embodiment, the operator also may have the opportunity to adjust the distribution based on input from the patient. For example, if the patient complains of pain in their big (great) toe, then the desired pressure in that area could be reduced by the operator, as illustrated in FIG. 10.

Figure 5:
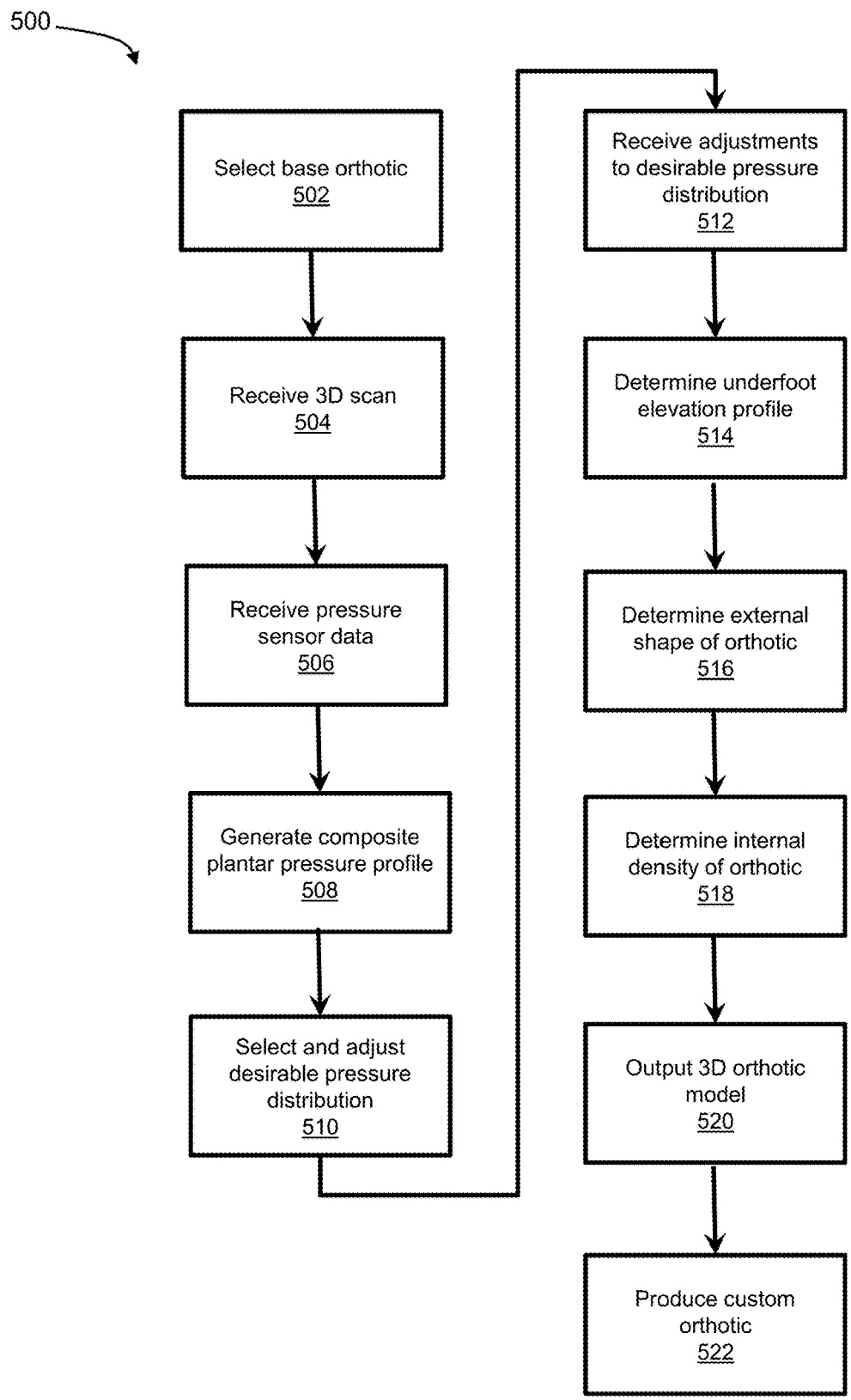
FIG. 5 is a flowchart of a method for designing of a custom foot orthotic, in accordance with an embodiment.
Figure 7:
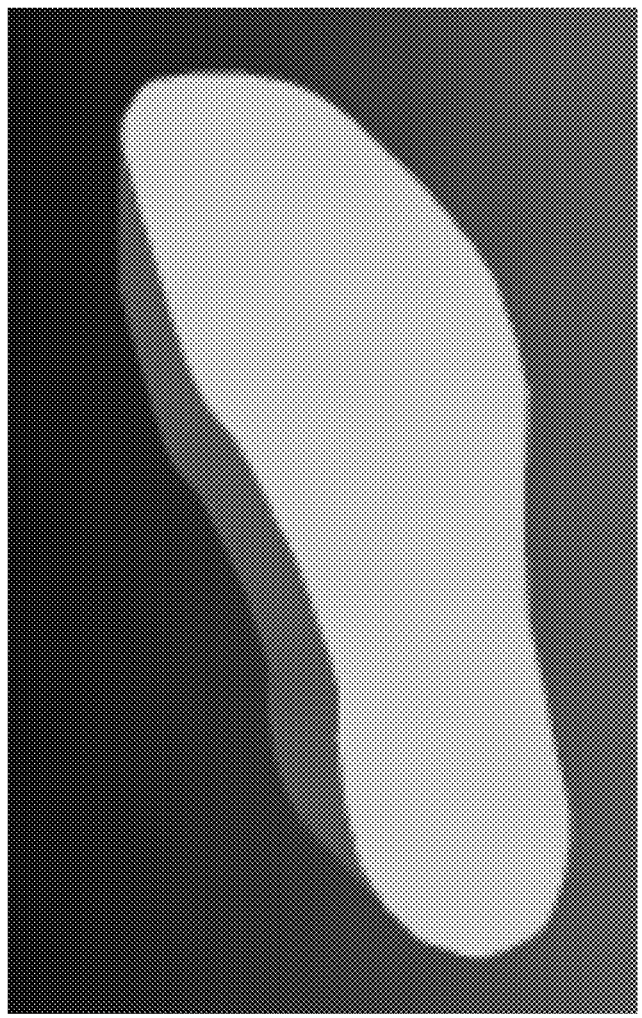
FIG. 7 illustrates an exemplary base orthotic model.

Referring now to FIG. 5, a method for designing of a custom foot orthotic 500 is shown. At block 502, as part of the input stage, in some cases, a 'base orthotic' can be selected by an operator. In a particular case, the operator can select a type of host shoe such that a base orthotic 3D model can be determined. This base orthotic provides an initial "block" of material from which the custom orthotic can be produced. Generally, different shoe types may require different 3D shapes to interface correctly with the respective insoles, and may restrict thickness in certain areas due to already small internal volumes. In an example, a set of candidate 3D base orthotics, labeled according to shoe type, brand, model, or the like, could be made available. In further cases, a generalized "base orthotic" may be used without selection by the operator. FIG. 7 illustrates an exemplary base orthotic model. In some cases, where there are multiple manufacturing technologies available to produce the orthotic, the operator can select their desired manufacturing technology because it may play a role in the orthotic design with respect to determining the internal density of the orthotic.

Figure 6:
FIG. 6 illustrates an exemplary 3D scan of a foot.

At block 504, the scanning data module 104 receives 3D scan(s) of one or both of the patient's feet from the 3D scanner 150. Any suitable 3D scanner can be used that is capable of scanning the foot and developing a composite set of 3D points that makes up the underfoot surface. For example, the Microsoft™ Kinect™ and its associated API, can be used to develop a scene scan of a foot within its view and outputs a set of 3D points describing the scene. A 3D model of this data can be readily received by the scanning data module 104. FIG. 6 illustrates an exemplary foot scan captured using a 3D scanner 150. In an exemplary case, it may be advisable to have the patient's foot applied to a flat, transparent surface with a mild amount of pressure to help them flatten their foot as they would when stepping or standing. Other configurations of the patient's foot while being scanned are contemplated. In some cases, during the scan, it may also be preferential to move the camera in a semi-circular fashion around the foot to capture various angles of the foot. In some cases, it may be preferential to record the scan using multiple cameras with different viewpoints. The above techniques may allow the fusion of surface points to be cleaner and more rounded at the edges of the foot.

The scanning data module 104 can automatically separate the 3D scan of the foot from any other objects in the scene; for example, by examining proximity to the 3D camera. In some cases, besides scanning the foot, it is possible that there will be 3D points that correspond to other objects in the scene, such as legs, clothing, or other items within the viewing range of the 3D camera. If, relative to the foot, the 3D scanner is located in a fixed position, or on a semi-circular track as described above, the foot can be separated using a 3D envelope. For example, if a point in question falls within a certain or predetermined "box" of space, the system 100 keeps it and, otherwise, discards it. In some cases, the footprint surface can also be lightly smoothed to correct for fusion errors.

Figure 4:
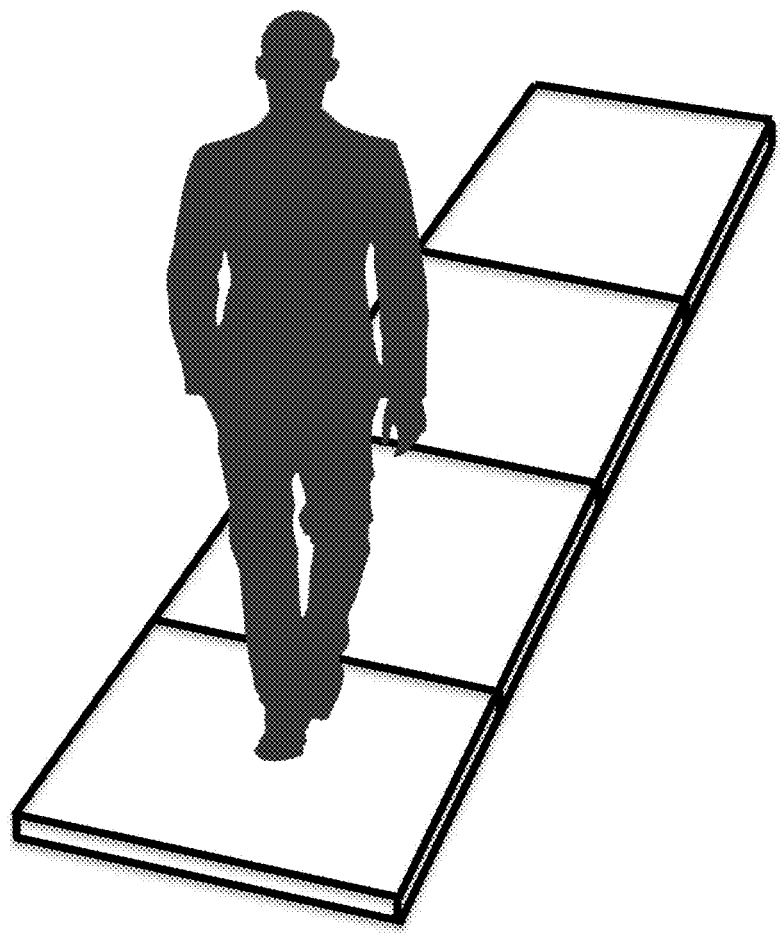
FIG. 4 diagrammatically illustrates a plantar pressure sensor array associated with a walkway.
Figure 8:
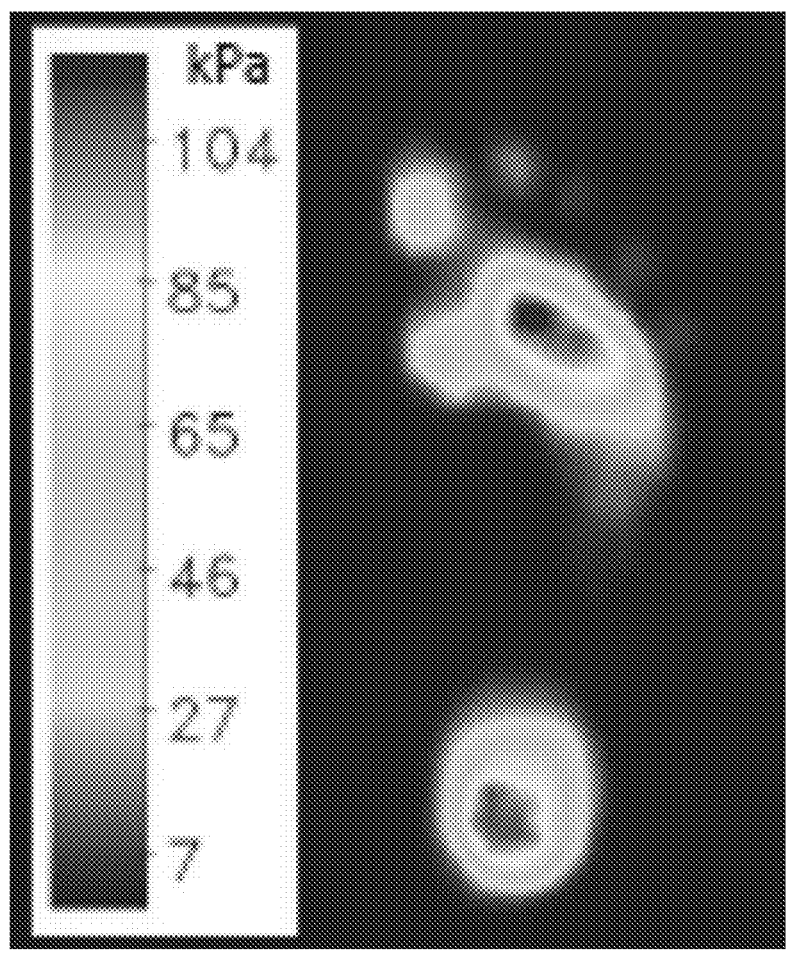
FIG. 8 illustrates an exemplary plantar pressure scan.

At block 506, the pressure data module 106 can record, and in some cases, preprocess data received from the plantar pressure sensor array 160. The plantar pressure sensor array 160 can be any suitable plantar pressure measurement device. In an example, the plantar pressure sensor array 160 can be associated with a walkway, for example, a device having grids of pressure sensors, with between-sensor distances as low as, for example, 5 mm, and that has recording of underfoot pressures at rates of, for example, 100 Hz and more. For example, a medical-grade, high-resolution walkway produced by Stepscan Technologies Inc. that is diagrammatically illustrated in FIG. 4. FIG. 8 illustrates an exemplary plantar pressure scan received from the plantar pressure sensor array 160. The pressure sensor array 160 communicates the plantar pressure sensor data to the pressure data module 106, and that data can be saved, for example, in a common container format (e.g., HDF5). In some cases, for example where the custom orthotic is meant to alleviate high-pressures or pain experienced during walking, the plantar pressure sensor array 160 can receive gait sensor readings while the patient walks across the grid of sensors walkway between 5 to 10 times. In this way, there can be enough footstep readings to generate a statistically reliable average footstep; in accordance with the preprocessing described below. In further cases, for example, the custom orthotic can assist in standing only and the plantar pressure sensor array 160 can be associated with a platform onto which the patient stands. This is beneficial if a smaller active sensor area is preferred to reduce cost. In this case, 5 to 10 recordings of short-duration standing on the platform having a grid of sensors may be used as plantar pressure readings.

At block 508, the pressure data module 106 can generate a composite plantar pressure profile from the multiple recorded footsteps or stances in the plantar pressure data received from the plantar pressure sensor array 160. Using image processing techniques (for example, image registration) to superimpose multiple footprints, an average or maximum pressure image or map may be directly computed to represent the typical plantar pressure profile of the foot.

At block 510, the pressure data module 106 can establish a desirable pressure distribution. Generally, a goal of custom orthotics as an intervention is to redistribute underfoot pressures, thus restoring the plantar pressure distribution to a more comfortable or healthy state. In view of this goal, the desirable pressure distribution may be established taking a variety of forms. For example, it may be desirable to have a flat or uniform pressure distribution, to generally improve comfort. In another example, the desirable pressure distribution may have a "healthy" pressure distribution. To determine the "healthy" pressure distribution for the unique patient's foot, a generic healthy distribution, for example an average pressure distribution calculated over a significant sample of patients, can be used. In this case, the "healthy" pressure distribution can be pressure-scaled and fitted to the patient's pressure map using a deformation algorithm. Other suitable variations of the desirable pressure distribution can be used, and in some cases, multiple options for the desirable pressure distribution may be offered and selected by the operator. As described below, the system 100 will automatically make location-specific adjustments to the orthotic's density to make the orthotic's pattern of support match the above desirable pressure distribution.

It is recognized that not all foot discomfort may be the result of abnormally high pressures in one area or another. Rather, a patient's foot may be abnormally sensitive in one area or another. At block 512, the pressure data module 106 can receive, via the input module 102, adjustments to the desirable pressure distribution from the operator. In this way, the operator can manually adjust the desirable pressure distribution to reduce pressures in areas where the patient reports discomfort. The input module 102 user interface could take any suitable form; for example, it may include an image of the automatically generated desirable pressure distribution. The operator can then select areas where pressure is to be reduced or increased.

As part of the design stage, at block 514, the model generation module 108 can generate an underfoot elevation profile. Provided the 3D foot shape describing the elevation of the foot from the scanning data module 104, the base orthotic, and in some cases the desirable pressure distribution from the pressure data module 106, the model generation module 108 can determine an elevation profile of the foot-interfacing surface of the base orthotic to support the desirable pressure distribution. In an example embodiment, the model generation module 108 can make the elevation profile relative to the foot-shape elevation profile, without necessarily explicitly considering the desirable pressure distribution. In another exemplary embodiment, the model generation module 108 can start with the base orthotic shape and lower the elevation profile in areas where a reduction in pressure is desired and increase the elevation profile where an increase in pressure is needed. In some cases, increases and decreases to the elevation profile may be controlled in an iterative feedback loop, such as that described herein with respect to changes to density of the foot orthotic model. In this way, an initial elevation profile may be controlled by the 3D foot shape and base orthotic and then updated during the iterative repetitions; in some cases, at the same time that densities of the orthotic model are adjusted. In this embodiment, the base orthotic's maximum dimensions may constrain the elevation profile, and may guide which approach or combination of approaches the model generation module 108 uses to define the elevation profile.

In some cases, the model generation module 108 may automatically smooth the elevation profile to enhance the appearance of the final product. The purpose of the smoothing is generally to blend the edge of the foot shape with the selected base orthotic. In further cases, smoothing can be adjusted by the operator via the input device 140.

At block 516, the model generation module 108 can determine an external shape of the custom orthotic. The model generation module 108 automatically virtually positions and aligns the elevation profile to the surface of the selected base orthotic, and bends the underfoot elevation profile, as a foot would, to make sufficient contact. In further cases, the base orthotic may bend itself, or along with the elevation profile. The model generation module 108 then virtually lowers the elevation profile below the surface of the base orthotic. The model generation module 108 can then three-dimensionally difference, remove, or cut-out, from the base orthotic, the area of the elevation profile that is below the base orthotic's surface. In some cases, the model generation module 108 can apply finishing techniques to improve the orthotics surface appearance; for example, adjusting the height of the area around the edge of the orthotic to smoothly blend in with the elevation profile imprint. In some cases, the orthotic is no thicker than about 15 mm at its thickest point and no thinner than about 7 mm at its thinnest point.

To virtually position the elevation profile, X and Y (or 2D) coordinates of a geometric center of the elevation profile is virtually placed at the same location as a 2D geometric center for the base orthotic model. The elevation profile or the base orthotic shape can then be virtually rotated and shifted along the X-Y plane until the underfoot elevation profile overlaps the base orthotic and the gap between the perimeter of the underfoot elevation profile and the perimeter of the base orthotic is substantially proportionally uniform along the length of the perimeter of the underfoot elevation profile.

The vertical or Z coordinate of the elevation profile begins virtually spaced above the orthotic. The elevation profile then virtually descends until it comes to rest on a top surface of the base orthotic. In most cases, base orthotics will be flat; however, for those orthotics that are not flat, the points of the elevation profile are adjusted as though there were springs connected between neighbouring points to permit the minimal shift in their position until the underside of the elevation profile comes to rest on the top side of the base orthotic. Advantageously, this approach mimics the change in a foot's shape as if it were set onto the base orthotic. For example, the rear-foot area of the base orthotic may be perfectly flat, while the mid- and forefoot areas descend away from it at a very slight angle. The elevation profile should bend slightly between the mid-foot and rear-foot such that it comes to rest on the base orthotic in the same way that a physical foot would when applied to a physical base orthotic of the same shape.

Figure 3:
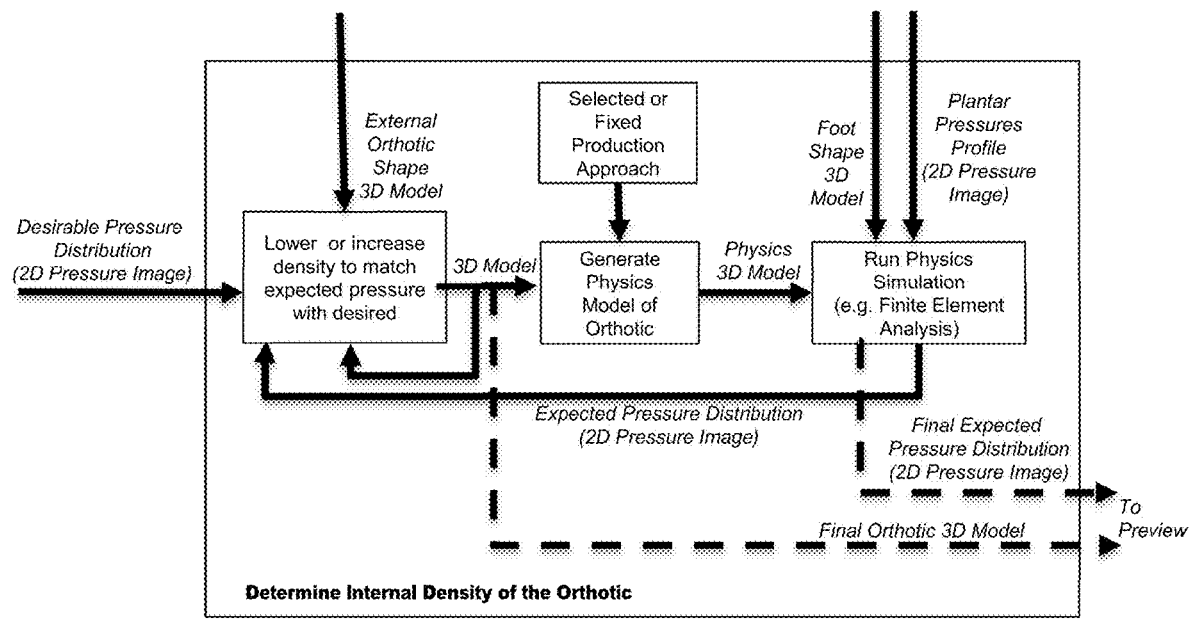
FIG. 3 is a diagram showing an exemplary approach for determining an internal density profile of the custom foot orthotic of the system of FIG. 1.

At block 518, as diagrammatically illustrated in FIG. 3, the model generation module 108 can determine an internal density profile of the custom orthotic. In a particular embodiment, the density profile determination is iterative. In an example, the model generation module 108 utilizes a physics simulation to determine the custom orthotic's expected pattern of support. In view of the pattern of support, the density of areas of the orthotic are lowered where the expected support is higher than the desired support, based on the desirable pressure distribution. The above can be iterated until an optimal density map has been identified; for example, where the last iteration did not improve or provide a better match of support than did the previous iteration.

The model generation module 108 lowers densities within the orthotic 3D model in areas where the expected pattern of support is greater than the appropriately superimposed desirable pressure distribution; in proportion to the difference between them. In some cases, variable densities may or may not be incurred through the entire thickness of the orthotic. For example, the orthotic may have full density on the top or bottom to improve resistance to wear or provide other beneficial qualities.

The model generation module 108 can convert the orthotic 3D model, with lowered densities, into a 3D physics model. In some cases, this can be based on the production technique. For example, a 3D printing technology called Fused Deposition Modeling (FDM) could be used to produce the physical orthotic. This production approach allows the operator to identify regions within the 3D model that have different infill densities. With this production approach, the model generation module 108 can quantize the proposed orthotic density map down to a reasonable set of different areas in the orthotic, for example six areas, in which to apply differing infill densities. In some cases, a "GCode" 3D printer formatted output can be converted back into a 3D model (".stl" format) and used accordingly. Advantageously, production of the foot orthotic in a homogeneous substrate with variable densities allows for kinematic correction without secondary application of glued on wedges or cushioning layers. A 3D variable density orthotic can advantageously limit degradation of product and maintain corrections over time.

The model generation module 108 can conduct a physics simulation; for example, a finite element analysis. In some cases, this approach can first create a virtual foot. For example, the patient's composite plantar pressure profile can be aligned and superimposed onto the scanned 3D foot shape, resulting in a map of downward force applied to a map of elevations which will interface with the custom orthotic model. The model generation module 108 can generate a physical 3D model of the foot surface using physical properties to govern a modelled representation of the ability of the 3D points in the foot shape to move relative their near neighbours. The physical properties can include physical properties of a generalized foot, for example foot elasticity, and foot mobility, the patient's plantar pressure data, and physical properties of the orthotic material (and its properties post-fabrication). Applied to this model will be the superimposed, downward forces determined in the plantar pressure profile. The physical simulation can be iterated until equilibrium is achieved. Initially, the virtual foot will come to rest on the surface of the virtual orthotic, and the orthotic will compress to some degree. In some cases, equilibrium is reached when the physically simulated models of the foot shape and the orthotic stop shifting and/or moving. The 3D model of the orthotic from the latest iteration is transformed into a physical model, for example, by creating finely-resolved, equally spaced nodes within the 3D envelope of the 3D model with simulated springs as interconnections between neighbouring nodes, where the spring properties are based on the elasticity and other physical properties of the orthotic material to be used in fabrication.

The resulting map of upward forces applied by the surface of the orthotic onto the foot shape, the expected pattern of support, is used to lower density as described above. When the expected pattern of support reaches an optimal point, for example, it is not more similar to the desirable pressure distribution than in the previous iteration, the expected pattern of support and the current orthotic model with lowered densities can be outputted.

Advantageously, the model generation module 108 uses the already collected 3D foot scan and plantar pressure profile to test and adjust the proposed orthotic model. This feedback loop ensures the desirable pressure distribution is achieved to the greatest extent possible having regard to the base orthotic shape and fabrication constraints.

Figure 9:
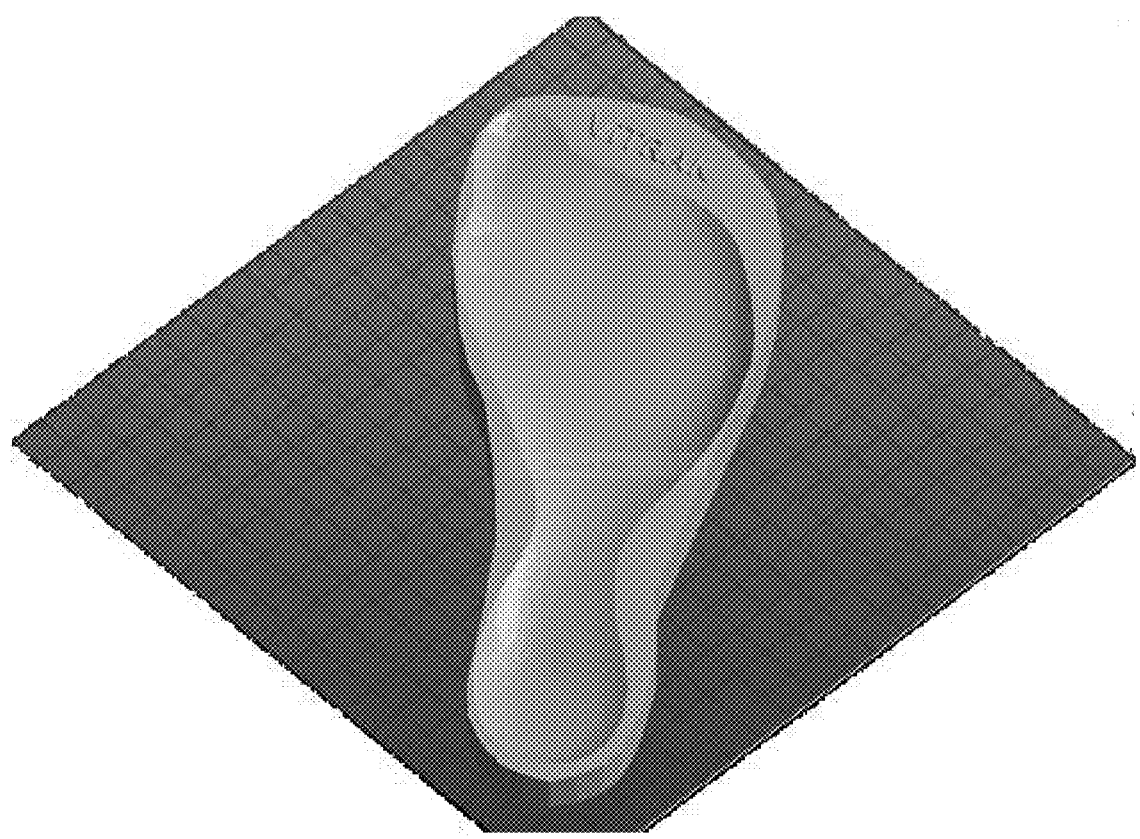
FIG. 9 illustrates an exemplary outputted custom orthotic model.

At block 520, as part of the production stage, the output module 110 outputs the resulting orthotic 3D model to the operator via the output device 170. FIG. 9 illustrates a graphical representation of an exemplary orthotic 3D model outputted to the output device 170. In some cases, the expected pressure distribution the orthotic will support, for comparison with the desirable pressure distribution, are also outputted to the operator. In some cases, metrics or metadata about the orthotic can be outputted to the operator. If the operator is satisfied with the expected performance of the orthotic, they can accept and initiate the production of the orthotic. In further cases, the system 100 will automatically initiate production of the orthotic without preview by the operator. In some cases, the system 100 can save the 3D model for later use or examination.

If the operator is unsatisfied by the above preview, they can return to the Input stage, where they may modify any or all of the inputs and request a redesign. This cycle can be repeated multiple times, according to the satisfaction of the operator. Advantageously, selection and adjustment of a desirable pressure distribution, and the decision of whether the expected orthotic is sufficient, is performable by those with varying levels of skill; and therefore, may be performable without the services of a professional or expert.

At block 522, where the output device 170 is a manufacturing environment, the output module 110 outputs the 3D model of the custom orthotic to the output device 170 for production of the custom orthotic. In some cases, the output module 110 may need to convert the file format to one useable by the manufacturing technology.

In the embodiments described herein, the orthotic model is matched to the desired pressure distribution by iteratively lowering the density of the orthotic. However, in further cases, another approach could include iteratively adjusting the thicknesses across the orthotic to arrive at a match to the desirable pressure distribution. Additionally, instead of lowering densities where orthotic support is too high, other strategies for adjusting the density can be used. For example, the approach can begin with an orthotic having a 50% material density over its entirety, and then increasing or decreasing densities to improve the match between the orthotic's support and the desirable pressure distribution.

In further embodiments, the custom orthotic can also be a hybrid of multiple types of materials or be produced using multiple fabrication technologies. Each material or fabrication technology having useful properties; for example, producing different densities, or producing certain pressure ranges or wear requirements that suit particular areas of the foot better than others.

An intended advantage of the embodiments described here is that the custom orthotic can be designed in a matter of minutes and likely would not require the operator to be provide any expert knowledge regarding custom orthotics, improving accessibility and lowering cost. The approach of the embodiments described herein is data-driven and reports on the expected support the custom orthotic can provide, thus empowering the operator to generate consistently effective results. In this way, advantageously, the custom orthotic is pre-fabrication testable via assessment of the 3D model prior to actual production of the custom orthotic. Additionally, the present embodiments described herein can employ a medical-grade plantar pressure measurement device and a 3D scanning device, thereby having the ability to achieve high and reliable accuracy in comparison to inaccurate insole recommendation devices or machines commonly found in pharmacies.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A system for designing of a custom foot orthotic for a patient, the system in communication with a plantar pressure sensor array, an input device, and an output device, the system comprising one or more processors and a data storage device, the one or more processors configured to execute:
    a pressure data module to receive plantar pressure scan data of the patient's foot from the plantar pressure sensor array and to establish a desirable pressure distribution;
    a model generation module to determine a custom internal density profile for a foot orthotic 3D model by iteratively superimposing the desirable pressure distribution over the foot orthotic 3D model and reducing or increasing portions of a density distribution over the foot orthotic 3D model based on the difference between an expected pattern of support and the desirable pressure distribution, the custom internal density profile determined based on a determination of an external shape of the custom foot orthotic; and
    an output module to output the foot orthotic 3D model to the output device, the output device using the foot orthotic 3D model to produce a physical manifestation of the custom foot orthotic having a customized infill density based on the custom internal density profile.

2. The system of claim 1, wherein the system is in further communication with a 3D scanner, the one or more processors further configured to execute a scanning data module to receive 3D scan data of the patient's foot from the 3D scanner, and wherein the model generation module further generates an underfoot elevation profile relative to an elevation profile of the patient's foot in the 3D scan data.

3. The system of claim 2, wherein the model generation module determines the foot orthotic 3D model of the custom foot orthotic by removing an area corresponding to the underfoot elevation profile from a base orthotic shape.

4. The system of claim 3, the one or more processors further configured to execute an input module to receive one or more input parameters from an operator via the input device, the one or more input parameters comprising a selection of the base orthotic shape.

5. The system of claim 4, wherein the one or more input parameters further comprise the desirable pressure distribution to be established.

6. The system of claim 1, wherein the expected pattern of support is determined using a physical simulation, where physical properties are used to generate a map of upward forces applied by a surface of the custom foot orthotic onto the patient's foot, the physical properties comprising physical properties of a generalized foot and material properties of the custom foot orthotic.

7. The system of claim 1, wherein adjustments to the desirable pressure distribution are received by the input module from an operator via the input device.

8. The system of claim 1, wherein the plantar pressure sensor array is associated with a walkway, and wherein the plantar pressure scan data is a composite of multiple foot pressure readings received while the patient was walking on the walkway.

9. The system of claim 1, wherein the plantar pressure sensor array is associated with a platform, and wherein the plantar pressure scan data is a composite of multiple foot pressure readings received while the patient was standing on the platform.

10. The system of claim 1, wherein the output device is a 3D printing device that produces the physical manifestation of the custom foot orthotic.

11. The system of claim 10, wherein the 3D printing device uses Fused Deposition Modeling to modify infill densities of a physical custom orthotic.

12. The system of claim 1, wherein the desirable pressure distribution is an average plantar pressure distribution calculated over a plurality of sample patients, the average plantar pressure distribution being pressure-scaled and fitted to plantar pressure scan data of the patient's foot.

13. A computer-implemented method for designing of a custom foot orthotic for a patient, the method comprising:
receiving plantar pressure scan data of the patient's foot;
establishing a desirable pressure distribution;
generating a custom internal density profile for a foot orthotic 3D model by iteratively superimposing the desirable pressure distribution over the foot orthotic 3D model and reducing or increasing density in regions of the foot orthotic 3D model based on the difference between an expected pattern of support and the desirable pressure distribution, the custom internal density profile determined based on a determination of an external shape of the custom foot orthotic;
outputting the foot orthotic 3D model; and
producing a physical manifestation of the custom foot orthotic having a customized infill density based on the custom internal density profile.

14. The method of claim 13, further comprising receiving 3D scan data of the patient's foot and generating an underfoot elevation profile relative to an elevation profile of the patient's foot in the 3D scan data.

15. The method of claim 14, further comprising determining the foot orthotic 3D model by removing an area corresponding to the underfoot elevation profile from a base orthotic shape.

16. The method of claim 15, further comprising receiving one or more input parameters from an operator, the one or more input parameters comprising a selection of the base orthotic shape.

17. The method of claim 16, wherein the one or more input parameters further comprise the desirable pressure distribution to be established.

18. The method of claim 13, wherein the expected pattern of support is determined using a physical simulation, where general physical properties of foot elasticity and physical properties of the orthotic material are used to generate a map of upward forces applied by a surface of the custom foot orthotic onto the patient's foot.

19. The method of claim 13, wherein the custom internal density profile is determined by iteration via successively comparing physical properties of a current expected pattern of support to the desirable pressure distribution until a current iteration does not provide a substantially better match between the current expected pattern of support and the desirable pressure distribution than a previous iteration.

20. The method of claim 13, further comprising receiving adjustments to the desirable pressure distribution from an operator.

21. The method of claim 13, wherein the plantar pressure scan data is a composite of multiple foot pressure readings received while the patient was walking.

22. The method of claim 13, wherein the plantar pressure scan data is a composite of multiple foot pressure readings received while the patient was standing.

23. The method of claim 13, wherein determining the foot orthotic 3D model of the custom foot orthotic comprises:
virtually positioning and aligning an underfoot elevation profile onto a surface of a base orthotic shape;
virtually lowering the underfoot elevation profile, along a vertical 'Z' axis, below the surface of the base orthotic shape such that the underfoot elevation profile at least partially resides inside of the base orthotic shape; and
removing areas of the base orthotic shape that encompass the same space as the underfoot elevation profile.

24. The method of claim 23, wherein positioning and aligning the underfoot elevation profile comprises:
virtually positioning 'X' and 'Y' coordinates of a geometric center of the underfoot elevation profile at the same location as 'X' and 'Y' coordinates of a geometric center of the base orthotic shape; and
virtually rotating and shifting the underfoot elevation profile or the base orthotic shape along respective 'X-Y' planes until the underfoot elevation profile overlaps the base orthotic and a gap between the perimeter of the underfoot elevation profile and the perimeter of the base orthotic is substantially proportionally uniform along the length of the perimeter of the underfoot elevation profile.

25. A custom foot orthotic customized to a patient and produced using a manufacturing environment based on a 3D model of the custom foot orthotic, the 3D model of the custom foot orthotic generated by one or more processors configured to execute:
a scanning data module to receive 3D scan data of the patient's foot from a 3D scanner;
a pressure data module to receive plantar pressure scan data of the patient's foot from a plantar pressure sensor array and to establish a desirable pressure distribution;
a model generation module to generate an underfoot elevation profile relative to an elevation profile of the patient's foot in the 3D scan data, the model generation module further generates a custom internal density profile of the 3D model of the custom foot orthotic by iteratively superimposing the desirable pressure distribution over the 3D model of the custom foot orthotic and reducing or increasing density in regions of the 3D model of the custom foot orthotic based on the difference between an expected pattern of support and the desirable pressure distribution, the custom internal density profile determined based on a determination of an external shape of the custom foot orthotic; and
an output module to output the 3D model of the custom foot orthotic to the manufacturing environment for production of the custom foot orthotic, the custom foot orthotic having a customized infill density based on the custom internal density profile.

* * * * *